United States Patent
Büge

(10) Patent No.: US 11,006,826 B2
(45) Date of Patent: May 18, 2021

(54) CALIBRATION METHOD FOR A CAMERA-BASED MEASURING DEVICE FOR DIAGNOSIS OF A HUMAN EYE

(71) Applicant: ALCON INC., Fribourg (CH)

(72) Inventor: David Büge, Potsdam (DE)

(73) Assignee: Alcon Inc., Fribourg (CH)

( * ) Notice: Subject to any disclaimer, the term of this patent is extended or adjusted under 35 U.S.C. 154(b) by 329 days.

(21) Appl. No.: 15/860,009

(22) Filed: Jan. 2, 2018

(65) Prior Publication Data

US 2018/0199812 A1 Jul. 19, 2018

(30) Foreign Application Priority Data

Jan. 18, 2017 (DE) .......................... 102017000452.8

(51) Int. Cl.
| | |
|---|---|
| *G06T 7/80* | (2017.01) |
| *A61B 3/14* | (2006.01) |
| *A61B 3/00* | (2006.01) |
| *A61B 3/117* | (2006.01) |

(52) U.S. Cl.
CPC .............. *A61B 3/14* (2013.01); *A61B 3/0025* (2013.01); *A61B 3/117* (2013.01); *G06T 7/80* (2017.01); *A61B 2505/05* (2013.01); *A61B 2560/0223* (2013.01); *G06T 2207/30041* (2013.01)

(58) Field of Classification Search
CPC .................................. A61B 3/14; A61B 3/0025
See application file for complete search history.

(56) References Cited

U.S. PATENT DOCUMENTS

| | | |
|---|---|---|
| 6,485,142 B1 | 11/2002 | Sheehy et al. |
| 2003/0020871 A1 | 1/2003 | Niven et al. |
| 2011/0134238 A1* | 6/2011 | Kotchou ................... G06T 7/80 348/140 |

(Continued)

FOREIGN PATENT DOCUMENTS

DE 102015001874 A1 8/2016

OTHER PUBLICATIONS

K. Murawski et al; "Method of Measuring the Distance to an Object Based on One Shot Obtained from a Motionless Camera with a Fixed-Focus Lens," ACTA Physica Polonica A: Series A, vol. 127, No. 6, Jun. 1, 2015 (Jun. 1, 2015), pp. 1591-1596, XP055467194, PL ISSN: 0587-4246, pp. 1592 -1594.

*Primary Examiner* — Jerry T Jean Baptiste
(74) *Attorney, Agent, or Firm* — Baker Botts LLP

(57) ABSTRACT

A calibration method for a camera-based measuring device comprises positioning a calibration object simulating an anterior region of the eye on a holder arranged movably in a first direction relative to a camera of the measuring device within a view field of the camera. The first direction is toward and away from the camera substantially along a camera axis. A motorized drive unit, in drive connection with the holder, is firstly controlled to drive the holder, with the calibration object positioned thereon in the camera view field, relative to the camera along the first direction at least once past a position of maximum definition of an image of the calibration object taken by the camera. A ratio between an actual size and an imaging size of the calibration object is determined on the basis of a camera image of the calibration object taken at the position of maximum definition.

8 Claims, 2 Drawing Sheets

(56) References Cited

U.S. PATENT DOCUMENTS

2011/0276042 A1* 11/2011 Dick ................. A61F 9/00814
 606/5
2014/0257258 A1   9/2014 Kurtz
2015/0301591 A1* 10/2015 Mueller ................. H04N 5/33
 345/156

* cited by examiner

CALIBRATION METHOD FOR A CAMERA-BASED MEASURING DEVICE FOR DIAGNOSIS OF A HUMAN EYE

CROSS REFERENCE TO RELATED APPLICATIONS

This application claims priority to German Patent Application Serial Number 102017000452.8, filed 18 Jan. 2017, titled "CALIBRATION METHOD FOR A CAMERA-BASED MEASURING DEVICE FOR DIAGNOSIS OF A HUMAN EYE," which is hereby incorporated by reference in its entirety.

TECHNICAL FIELD

The present disclosure relates generally to a calibration method for a camera-based measuring device for diagnosis of a human eye. It relates in particular to a method for the camera-based measuring device, by which the latter is calibrated for pre-operative diagnostic measurements in cataract surgery.

BACKGROUND

In (laser refractive) cataract surgery, the natural, clouded lens of a patient's eye is replaced by an artificial lens. For this purpose, the anterior chamber of the patient's eye is opened, the natural lens is removed, and, finally, an artificial lens is inserted at the position of the natural lens.

In the context of pre-operative diagnostics for cataract surgery, a high-resolution reference image of the patient's eye that is to be treated is taken in order to measure said eye. The reference image taken comprises, for example, scleral blood vessels, the limbus, and points of orientation on the iris of the patient's eye. From the reference image, it is possible to determine the position of incisions that are to be made and also to determine the positioning of the artificial lens that is to be inserted. The reference image forms the basis for calculating a plan for cataract surgery.

The reference image of the patient's eye is taken with a camera. Properties of the patient's eye, for example the limbus diameter, can be read out from the reference image by means of suitable image processing. For this purpose, a suitable calibration is needed so that it is possible, from the properties of the patient's eye depicted in the reference image, to reliably determine the actual properties, for example the actual limbus diameter of the patient's eye.

SUMMARY

It is an aim of the present invention to make available a reliable calibration for determining properties of a patient's eye, or of a test object, from a reference image thereof.

According to certain embodiments, a calibration method is provided for a camera-based measuring device for diagnosis of the human eye. The calibration method comprises a step in which a calibration object simulating an anterior region of the eye is positioned on a holder which is arranged movably in a first direction relative to a camera of the measuring device within a view field of the camera. The first direction is a direction toward and away from the camera substantially along a camera axis (for example along the optical axis of the camera). The calibration method moreover comprises a step in which a motorized drive unit, in drive connection with the holder, is firstly controlled to drive the holder, with the calibration object positioned thereon in the camera view field, relative to the camera along the first direction at least once past a position of maximum definition of an image of the calibration object taken by the camera. The calibration method moreover comprises a step in which a ratio between an actual size and an imaging size of the calibration object is determined on the basis of a camera image of the calibration object taken at the position of maximum definition.

The calibration, that is to say the determination of the calibration ratio between the actual size and the imaging size of the calibration object, is effected on the basis of the camera image taken at the position of maximum definition. The high definition permits a high degree of precision in determining the imaging size from the camera image, which determination is carried out, for example, by means of a suitable image-processing program (in an automated manner).

The calibration object simulating an anterior region of the eye can be configured in the form of a dome, for example in the form of a hemisphere. Thus, the dome-shaped surface of the calibration object can, for example, simulate a region of the human cornea. At least one predetermined diameter of the calibration object can be present as an actual size, which is correlated with a diameter that has been determined as an imaging size from the camera image taken at the position of maximum definition. The predetermined diameter of the calibration object can correspond, for example, to a customary limbus diameter. A value of between 7.0 mm and 10.0 mm can be provided for the predetermined diameter.

To reduce uncertainty when determining the imaging size and, therefore, to further improve the precision of the calibration, the first control step of the calibration method can comprise controlling the drive unit to drive the holder, with the calibration object positioned thereon in the camera view field, back and forth once or several times relative to the camera along the first direction and, in so doing, to drive it in each case past the position of maximum definition. Provision can be made here to determine the imaging size in each case from a plurality of camera images taken in the position of maximum definition (for example from each of these camera images of maximum definition). From the plurality of determined imaging sizes, an averaged imaging size can be calculated and can be used to determine the calibration ratio.

The human eye has specific properties for each patient. For example, the limbus diameter can vary between different patients. To take such variations into account in the calibration, provision can be made that the calibration method comprises repeating the steps of the first control and of the determination, in each case with a different size of calibration object positioned on the holder in the camera view field.

The holder can be arranged so as also to be movable relative to the camera in a second direction extending transversely with respect to the first direction. At least in this case, the positioning step can comprise positioning a plurality of calibration objects of different sizes alongside each other on the holder in the second direction. Moreover, the calibration method can comprise a second step of controlling the drive unit in order to bring the calibration objects positioned on the holder successively to a position within the view field of the camera. An alternating sequence of the first control and of the second control of the drive unit thus makes it possible to successively determine the imaging size from a camera image taken in the position of maximum definition initially for a first calibration object and then for the further calibration objects arranged on the holder along the second direction.

To calculate an actual object size of an object different than the plurality of calibration objects (for example of a test object or of a patient's eye), it may be necessary to determine the ratio of imaging size to actual size for an imaging object size different than the determined imaging sizes of the calibration objects. For this purpose, provision can be made that the calibration method comprises determining a calibration function on the basis of the determined ratios between the actual size and the imaging size of all the calibration objects, in particular by interpolation and/or extrapolation techniques, such that the calibration function makes available an actual object size for each of a plurality of different imaging sizes of an object.

BRIEF DESCRIPTION OF THE DRAWINGS

Further features, advantages and aspects of the present invention will become clear from the following description of the attached drawings, in which.

DETAILED DESCRIPTION OF EXEMPLARY EMBODIMENTS

Figure 1:
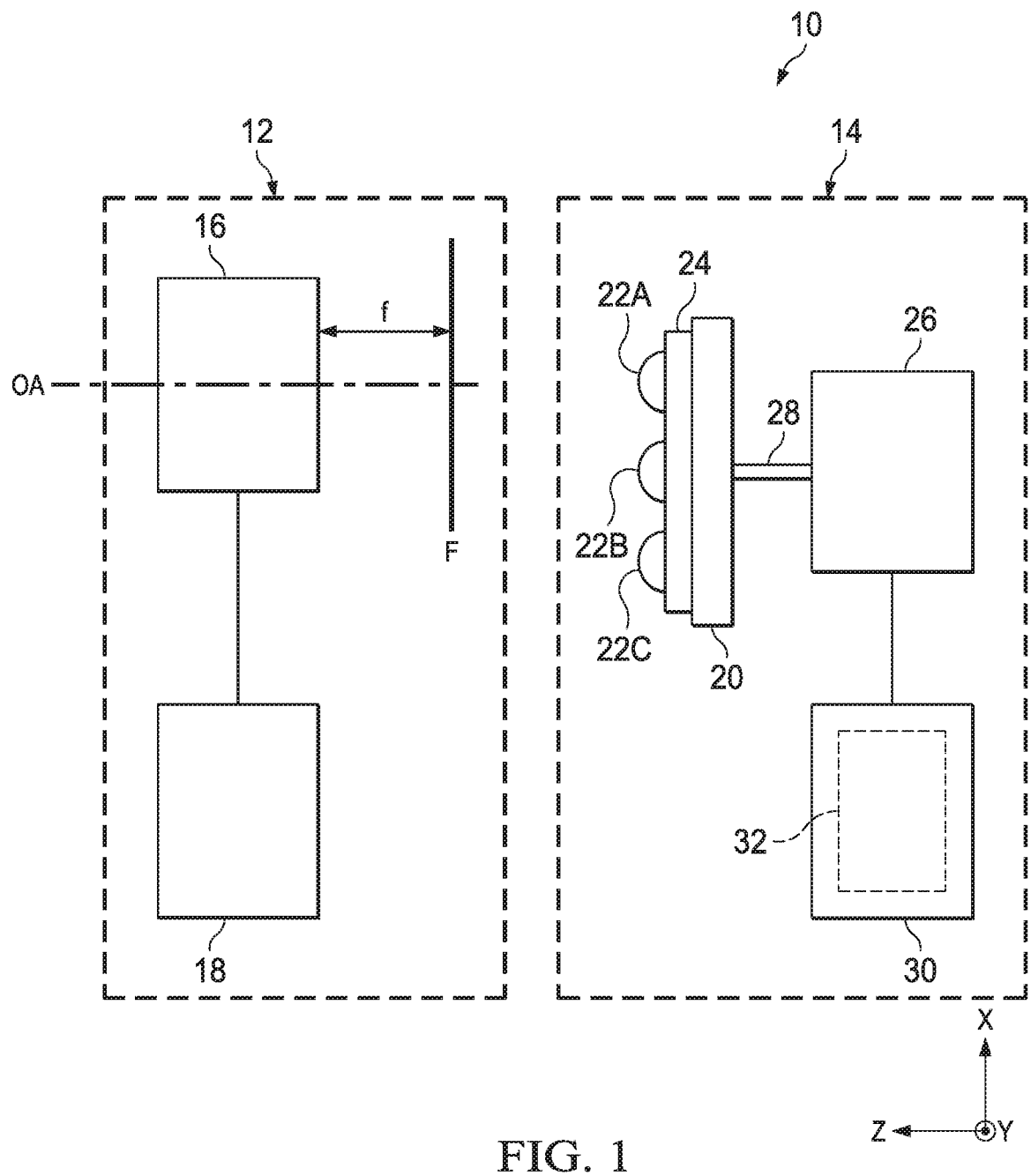
FIG. 1 shows a schematic block diagram of an exemplary embodiment of an arrangement for carrying out a calibration method for a camera-based measuring device for diagnosis of the human eye.
Figure 2:
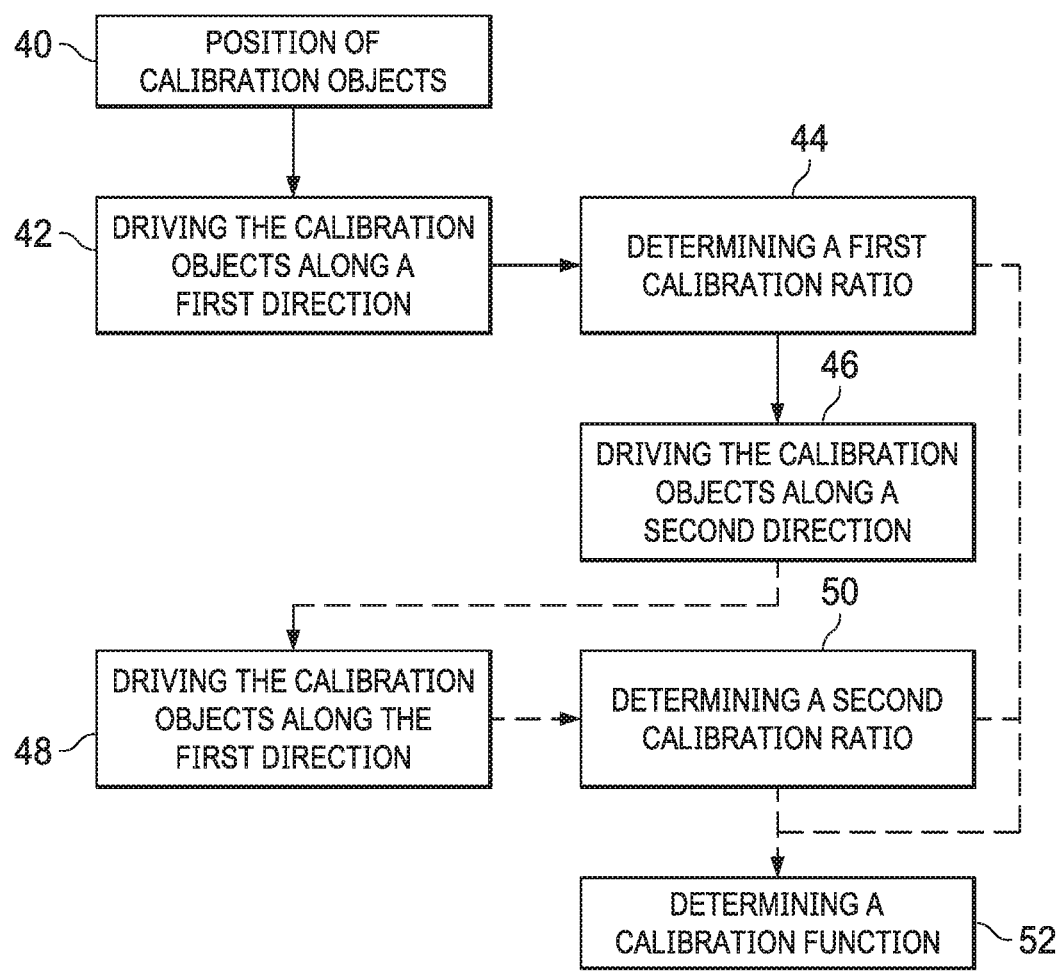
FIG. 2 shows a flow diagram of an exemplary embodiment of a calibration method for a camera-based measuring device for diagnosis of the human eye.

FIG. 1 shows, in a block diagram, an exemplary embodiment of an arrangement, generally designated by 10, for carrying out a calibration method (for example for carrying out the calibration method according to FIG. 2) for a camera-based measuring device 12 for diagnosis of the human eye. The arrangement 10 comprises the camera-based measuring device 12 and a calibration station 14.

The camera-based measuring device 12 comprises a camera 16, of which the optical axis is indicated by the broken line labeled OA in FIG. 1. A focal plane F designates an x-y plane which is oriented transversely with respect to the optical axis OA and in which images taken by the camera 16 have a maximum definition (focus). A distance f between a front lens (not shown) of the camera 16 and the focal plane F is designated below as the working distance of the camera 16.

In the exemplary embodiment shown in FIG. 1, provision is made that the camera 16 comprises a plurality of infrared (IR) light sources (not shown) (for example IR LEDs) for illuminating an object within the view field of the camera 16, and a sensor (not shown) for detecting reflected IR light. Alternatively or in addition to this, the camera 16 can be provided with at least one light source for illuminating the object with light in the visible wavelength range and with a sensor for detecting reflected light in the visible wavelength range.

The camera-based measuring device 12 according to the exemplary embodiment shown in FIG. 1 moreover comprises a processing unit 18 for evaluating images taken by the camera 16, particularly in respect of predetermined features. The evaluation can be performed using a suitable image-processing program. The processing unit 18 can moreover comprise a display (not shown), on which images taken by the camera 16 and/or results of the evaluation of the images are displayed.

The calibration station 14 comprises a holder 20, which is designed for the arrangement of a plurality of calibration objects, generally designated by 22. According to the exemplary embodiment shown in FIG. 1, three calibration objects 22A, 22B, 22C mounted on a carrier 24 are received by the holder 20 or arranged on the holder 20. In another exemplary embodiment, provision can be made that the holder 20 is designed to receive, or to have arranged on it, a number of calibration objects 22 other than three (e.g. just a single calibration object 22). The holder 20 can be designed, for example, as a carriage that is movable at least in one direction.

The calibration objects 22 simulate an anterior region of a human eye. For this purpose, the calibration objects 22 shown in FIG. 1 are in the shape of a hemisphere. The calibration objects 22 have different diameters, which are within the range of values of typical limbus diameters of the human eye. For example, provision can be made that the three calibration objects 22A, 22B, 22C have a diameter of 9.5 mm, 8.5 mm and 7.5 mm, respectively.

In the present exemplary embodiment, the calibration objects 22 (e.g. made of darkened glass) stand out in their color from the carrier 24 (e.g. made of white plastic material). Therefore, when illuminated with IR light or with light in the visible wavelength range, the calibration objects 22 also stand out from each other in their color in an image taken by the camera 16. By means of the processing unit 18, the calibration objects 22 or their contours can be identified in an image taken by the camera 16.

The calibration station 14 moreover comprises a drive unit 26, which is connected to the holder 20 by a mechanical drive connection indicated at 28. The drive unit 26 is designed to drive or adjust the position of the holder 20 at least along a first direction designated as the z direction. For this purpose, the drive unit 26 can, for example, contain an electromotive drive assembly.

The drive unit 26 is controlled by a control unit 30 of the calibration station 14. The control unit 30 is program-controlled, for example, and can for this purpose contain a memory 32 with instructions stored therein, in accordance with which the holder 20 is to be driven. Provision can be made for the processing unit 18 of the measuring device 12 and the control unit 30 of the calibration station 14 to be provided as an individual component. At least in this case, the control unit 30 can have an electrical signal link to the camera 16, in order to control an illumination and/or an imaging by means of the camera 16.

As is depicted schematically in the arrangement 10 shown in FIG. 1, the calibration objects 22 arranged on the holder 20 are positioned within a plane transverse to the optical axis OA of the camera 16. When the holder 20 is driven in the z direction, the calibration objects 22 are to be moved in the direction of the camera 16. If a distance between the calibration objects 22 and the front lens of the camera 16 corresponds to the working distance f, the calibration objects 22 are located within the focal plane F of the camera 16, i.e. in the position of maximum definition. The calibration objects 22 can be moved in and out of a view field (not shown in FIG. 1) of the camera 16, by means of the holder 20 being driven relative to the camera 16 (manually or by means of the drive unit 26) along a second direction (the x direction) that extends transversely with respect to the optical axis.

FIG. 2 shows the steps of an exemplary embodiment of a calibration method for a camera-based measuring device for diagnosis of the human eye, for example for the camera-based measuring device 12 described with reference to FIG. 1.

In a first step 40, at least one calibration object simulating an anterior region of the eye is positioned within a view field of a camera. Here, provision can be made for the calibration objects 22 described with reference to FIG. 1 to be positioned along the x direction extending transversely with respect to the optical axis of the camera 16 (e.g. on the carrier 24 oriented in the x direction), such that one of the calibration objects 22 arranged on the holder 20 (for example the calibration object 22A) is located within the view field of the camera 16, while the other calibration objects 22 received by the holder 20 (for example the calibration objects 22B and 22C) are positioned outside the view field of the camera 16. In particular, the calibration object 22A positioned within the view field of the camera 16 can be arranged on the optical axis of the camera 16.

In a following step 42 of the calibration method according to FIG. 2, a motorized drive unit 26 (see FIG. 1) is controlled in order to drive the calibration objects 22 along a first direction relative to the camera. For example, the calibration objects 22 are moved toward the camera 16 in the z direction by means of the drive unit 26 included in the calibration station 14 according to FIG. 1. A distance between the front lens of the camera 16 and the calibration object 22A positioned within the view field of the camera 16 is reduced beyond the working distance f of the camera 16. Before and/or after the described movement, the calibration objects 22 are moved away from the camera 16 counter to the z direction. The camera 16 is designed, at least during a phase of the movement, to continuously take images of the calibration object 22A positioned within the view field of the camera 16.

Provision can be made to control the driving of the calibration objects 22 along the first direction within a predefined interval by an expected working distance f of the camera 16. Thus, the expected working distance f can be about 17 cm for example, and the distance between the front lens of the camera 16 and the calibration object 22A positioned within the view field of the camera 16 can be varied within the range of 17 cm+/−5 cm.

In a further step 44, a first calibration ratio between an actual size and an imaging size of the (first) calibration object 22A positioned in the view field of the camera 16 is determined on the basis of at least one camera image of the calibration object 22A taken at the position of maximum definition. For this purpose, the camera image or camera images are first of all determined in which, when they are taken, the calibration object 22A is located in the focal plane F of the camera 16. For this purpose, for example, a gradient between the image of the calibration object 22A and of the area of the carrier 24 (see FIG. 1) surrounding the calibration object 22A can be evaluated. Alternatively or in addition to this, it is possible to determine a circumference or a radius of the reflections, visible in the image of the calibration object 22A, of the lighting means with which the camera 16 illuminates the calibration object 22A. The definition of the images taken by the camera is maximized in the focal plane F of the camera 16. Accordingly, the evaluation of the camera image of maximum definition shows a maximum gradient or a minimal reflection circumference or reflection radius.

From the camera image or camera images of maximum definition, it is possible to read out imaging features, for example to determine an imaging size of the calibration object 22A positioned within the view field of the camera 16. In particular, a diameter of the calibration object 22A is determined as imaging size from the camera image or the camera images of maximum definition and is correlated with the actual diameter (actual size) of the calibration object 22A.

If the calibration object 22A is moved several times past the position of maximum definition by means of the drive unit (for example by being driven several times in the z direction and counter to the z direction), an imaging size can be determined from each camera image of maximum definition that is taken during this process. From the determined imaging sizes, an averaged imaging size of the calibration object 22A can be calculated in order to use this to determine the first calibration ratio (step 44).

Provision can be made that the evaluation of the camera images in terms of the position of maximum definition and/or in terms of the imaging size of the calibration object 22A is carried out by means of a suitable image-processing program. The processing unit 18 in the camera-based measuring device 12 according to FIG. 1 can include such an image-processing program.

In a further (optional) step 46, the motorized drive unit 26 (see FIG. 1) is controlled in order to drive the calibration objects 22 relative to the camera 16 along a second direction transverse to the optical axis OA of the camera 16. Thus, the calibration object 22A shown in FIG. 1 and positioned in the view field of the camera 16 is moved in the x direction out of the view field of the camera 16, and the calibration object 22B arranged next to the calibration object 22A counter to the x direction is moved into the view field of the camera 16. Provision can be made to drive the calibration objects 22 along the second direction until the calibration object 22B is positioned on the optical axis OA of the camera 16. For this purpose, the calibration objects 22 can, for example, be positioned with a defined spacing (for example the known spacing between their dome vertices) along the second direction.

With reference to FIG. 1, provision is made that the driving of the calibration objects 22 in accordance with steps 42 and 46 can be effected according to stored instructions by the control device 30. Alternatively to this, the driving in accordance with step 46 can be effected manually for example.

In the subsequent step 48, the above-described step 42 of driving the calibration objects along the first direction is repeated with the calibration objects in the positioning that is present after step 46. Moreover, in step 50, a second calibration ratio is determined for the calibration object (for example the calibration object 22B according to FIG. 1) positioned in the view field of the camera. With reference to FIG. 1, after steps 40 to 50 of the method according to FIG. 2 have been carried out, there is in each case an (e.g. averaged) calibration ratio for the calibration objects 22A and 22B. In an alternative exemplary embodiment, provision can be made to determine a calibration ratio for a larger number of calibration objects 22 (e.g. for the three calibration objects 22A, 22B and 22C).

When steps 46 to 50 of the method according to FIG. 2 are carried out (as indicated by the broken arrows), it is possible, in a further step 52, to determine a calibration function on the basis of the plurality of determined calibration ratios between actual size and imaging size of the calibration objects. For this purpose, interpolation and/or extrapolation techniques are used in order to provide an actual object size for each of a plurality of different imaging sizes of an object. For example, a linear interpolation can be performed between determined calibration ratios. Provision can be made that the processing unit 18 according to FIG. 1 is configured to determine such a calibration function.

The calibrated measuring device 12 can thus be used to measure objects of varying actual size. Thus, properties of a test object (e.g. in the manner of the calibration objects 22 according to FIG. 1) or of a patient's eye can be evaluated. For example, provision can be made to determine a limbus diameter or a pupil diameter from an image taken by means of the camera 16 of the measuring device 12.

The invention claimed is:

1. A calibration method for a camera-based measuring device for diagnosis of a human eye, said method comprising:

positioning a calibration object simulating an anterior region of the eye on a holder which is arranged movably in a first direction relative to a camera of the measuring device within a view field of the camera, wherein the first direction is a direction toward and away from the camera along a camera axis;

firstly controlling a motorized drive unit, which is in drive connection with the holder, to drive the holder, with the calibration object positioned thereon in the camera view field, relative to the camera along the first direction at least once past a position of maximum definition of an image of the calibration object taken by the camera; and determining a ratio between an actual size and an imaging size of the calibration object on the basis of a camera image of the calibration object taken at the position of maximum definition.

2. The calibration method as claimed in claim 1, wherein the first control step comprises controlling the drive unit to drive the holder, with the calibration object positioned thereon in the camera view field, back and forth once or several times relative to the camera along the first direction and, in so doing, to drive it in each case past the position of maximum definition.

3. The calibration method as claimed in claim 1, comprising:

repeating the steps of the first control and of the determination, in each case with a different size of calibration object positioned on the holder in the camera view field.

4. The calibration method as claimed in claim 3, wherein the holder is arranged so as also to be movable relative to the camera in a second direction extending transversely with respect to the first direction, wherein the positioning step comprises positioning a plurality of calibration objects of different sizes alongside each other on the holder in the second direction, and wherein the method comprises a second step of controlling the drive unit in order to bring the calibration objects positioned on the holder successively to a position within the view field of the camera.

5. The calibration method as claimed in claim 3, further comprising:

determining a calibration function on the basis of the determined ratios between the actual size and the imaging size of all the calibration objects, wherein the calibration function makes available an actual object size for each of a plurality of different imaging sizes of an object.

6. The calibration method as claimed in claim 5, wherein the calibration function is determined on the basis of the determined ratios between the actual size and the imaging size of all the calibration objects by interpolation and/or extrapolation techniques.

7. The calibration method as claimed in claim 4, further comprising:

determining a calibration function on the basis of the determined ratios between the actual size and the imaging size of all the calibration objects, wherein the calibration function makes available an actual object size for each of a plurality of different imaging sizes of an object.

8. The calibration method as claimed in claim 2, comprising:

repeating the steps of the first control and of the determination, in each case with a different size of calibration object positioned on the holder in the camera view field.

* * * * *